US005500012A

United States Patent [19]
Brucker et al.

[11] Patent Number: 5,500,012
[45] Date of Patent: Mar. 19, 1996

[54] ABLATION CATHETER SYSTEM

[75] Inventors: Gregory G. Brucker, Minneapolis; Steven D. Savage, Brooklyn Center, both of Minn.

[73] Assignee: Angeion Corporation, Plymouth, Minn.

[21] Appl. No.: 272,268

[22] Filed: Jul. 8, 1994

Related U.S. Application Data

[63] Continuation of Ser. No. 913,380, Jul. 15, 1992, abandoned.

[51] Int. Cl.⁶ .................................................. A61B 17/36
[52] U.S. Cl. .............................. 607/122; 128/642; 606/7; 606/15; 604/22
[58] Field of Search ...................... 606/7, 13–16; 128/642; 607/89, 115, 116, 122; 604/22

[56] References Cited

U.S. PATENT DOCUMENTS

| | | | |
|---|---|---|---|
| 4,576,177 | 3/1986 | Webster, Jr. | 606/7 |
| 4,660,571 | 4/1987 | Hess et al. | 606/15 |
| 4,699,147 | 10/1987 | Chilson . | |
| 4,762,120 | 8/1988 | Hussein . | |
| 4,784,133 | 11/1988 | Mackin | 606/7 |
| 4,785,815 | 11/1988 | Cohen | 606/7 |
| 4,813,425 | 3/1989 | Malis . | |
| 4,819,630 | 4/1989 | DeHart . | |
| 4,850,351 | 7/1989 | Herman et al. . | |
| 4,854,315 | 8/1989 | Stack et al. | 606/7 |
| 4,860,743 | 8/1989 | Abela . | |
| 4,862,887 | 9/1989 | Weber . | |
| 4,890,898 | 1/1990 | Bentley . | |
| 4,940,064 | 7/1990 | Desai | 128/786 |
| 4,985,028 | 1/1991 | Isner et al. | 606/15 |
| 5,053,033 | 10/1991 | Clarke . | |
| 5,083,565 | 1/1992 | Parins . | |
| 5,106,387 | 4/1992 | Kittrell et al. . | |
| 5,125,896 | 6/1992 | Hojeibane . | |
| 5,156,151 | 10/1992 | Imran | 128/786 |
| 5,169,396 | 12/1992 | Dowlatshahi . | |
| 5,188,635 | 2/1993 | Radkte . | |
| 5,209,748 | 5/1993 | Daikuzono . | |
| 5,281,212 | 1/1994 | Savage et al. | 606/15 |

FOREIGN PATENT DOCUMENTS

| | | |
|---|---|---|
| 0422363 | 4/1991 | European Pat. Off. . |
| 0428812 | 5/1991 | European Pat. Off. . |
| 0481684 | 4/1992 | European Pat. Off. . |
| 0500215 | 8/1992 | European Pat. Off. . |

*Primary Examiner*—Stephen C. Pellegrino
*Assistant Examiner*—Michael Peffley
*Attorney, Agent, or Firm*—Patterson & Keough

[57] ABSTRACT

An ablation catheter system, including a guiding/mapping catheter assembly and a laser catheter. The guiding/mapping catheter includes ring electrodes, tip electrodes, a moveable fixation wire, and a central catheter lumen for an ablation catheter. A laser catheter includes an optical fiber for passing laser energy, tip electrodes, an optical fiber port, and thermocouples on the end of hypodermic tubing.

24 Claims, 5 Drawing Sheets

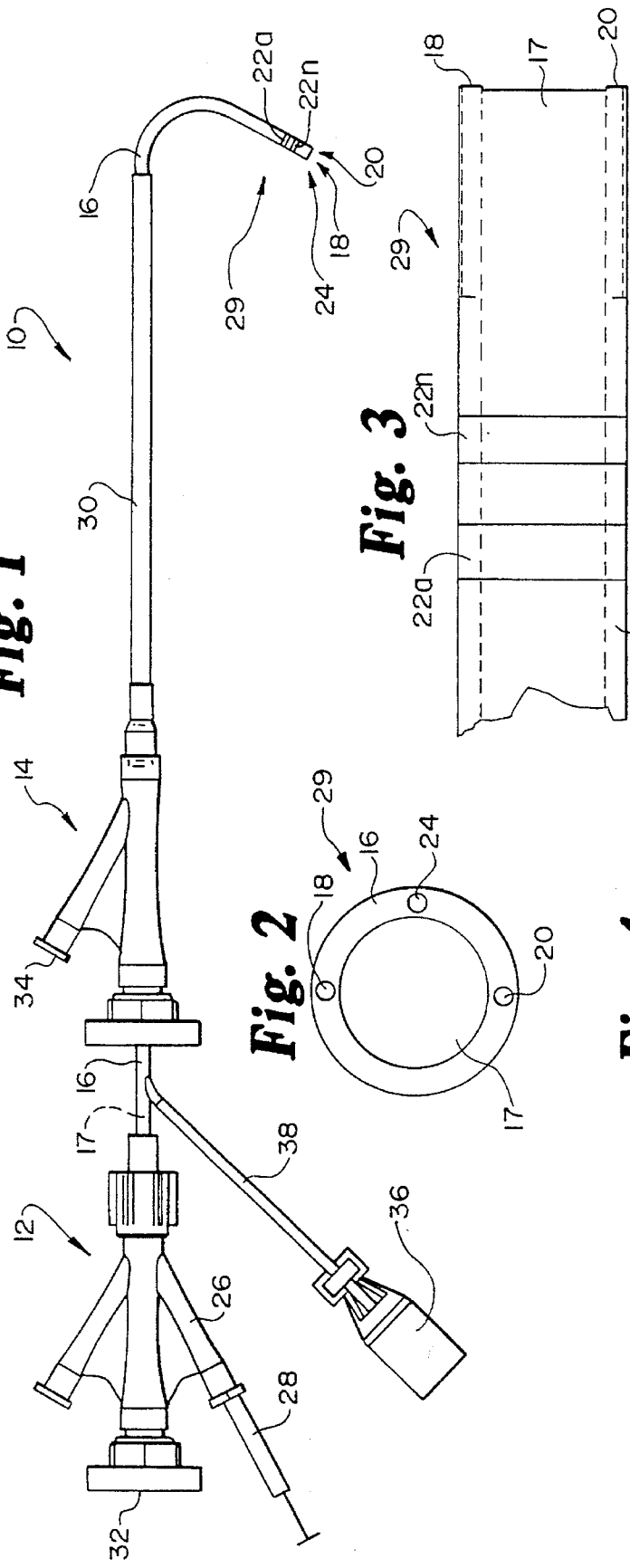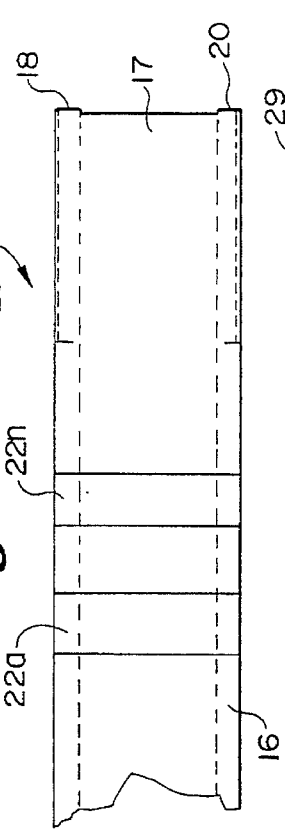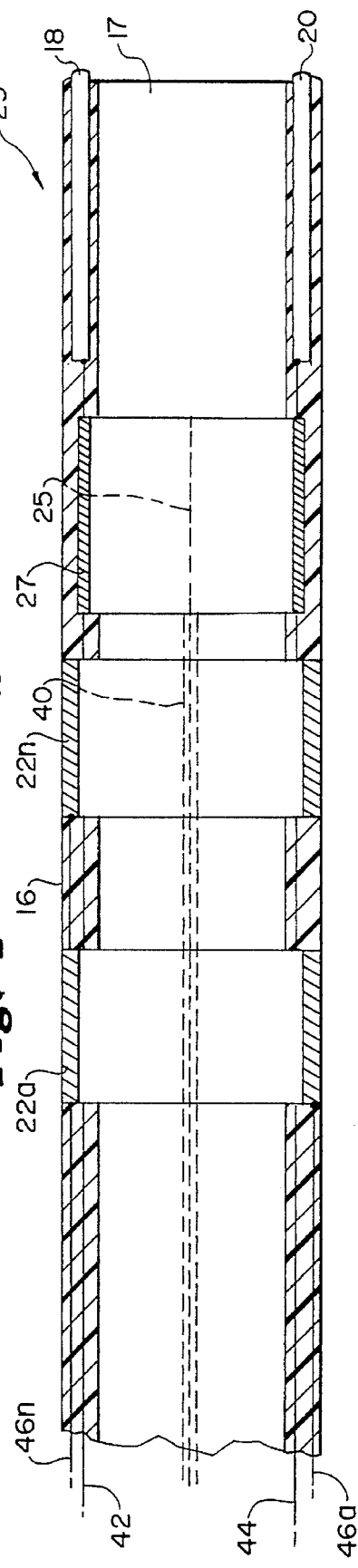

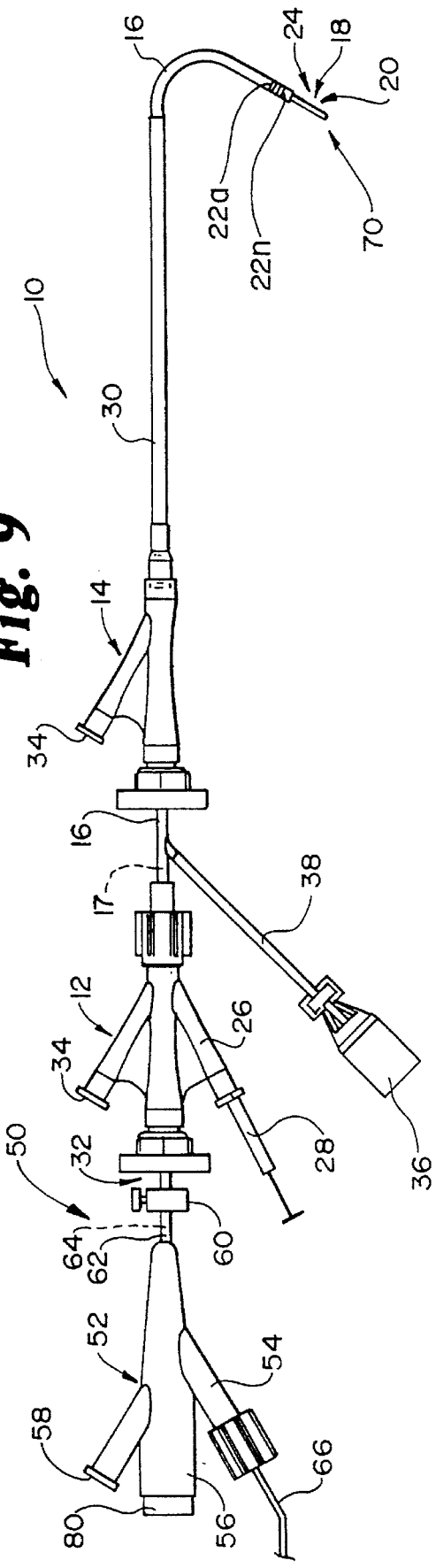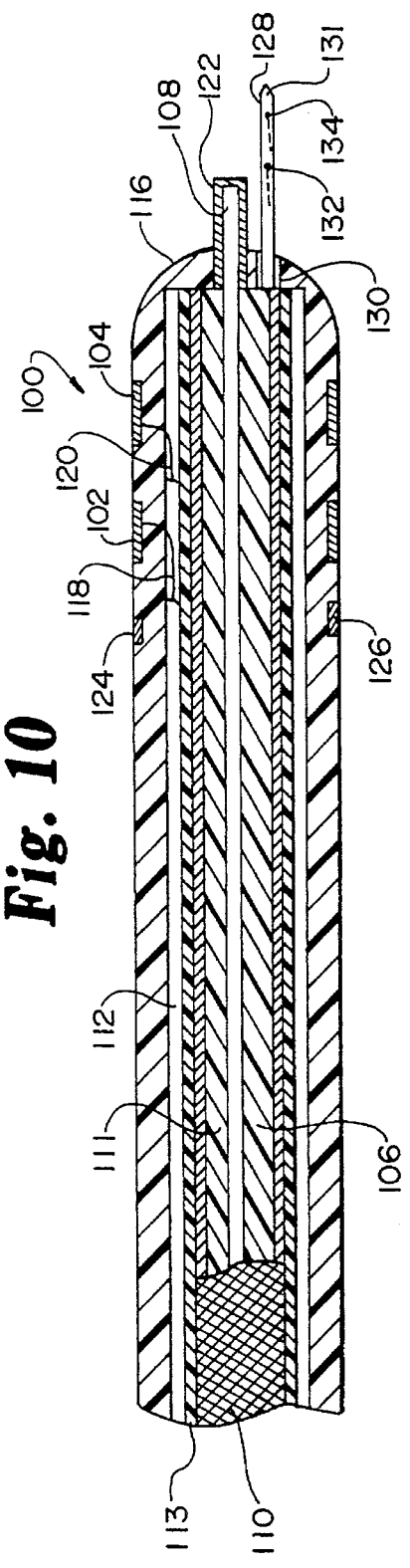

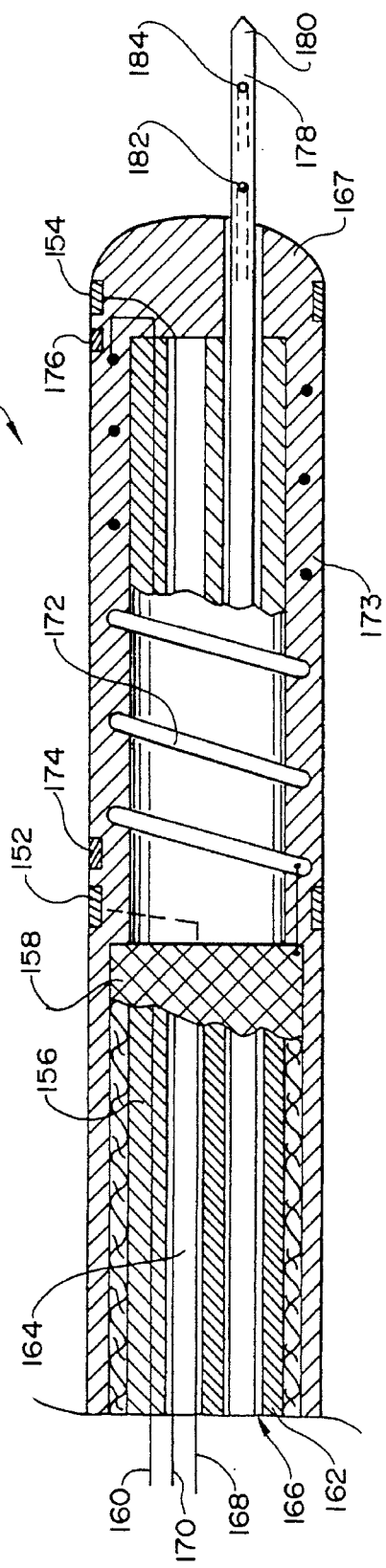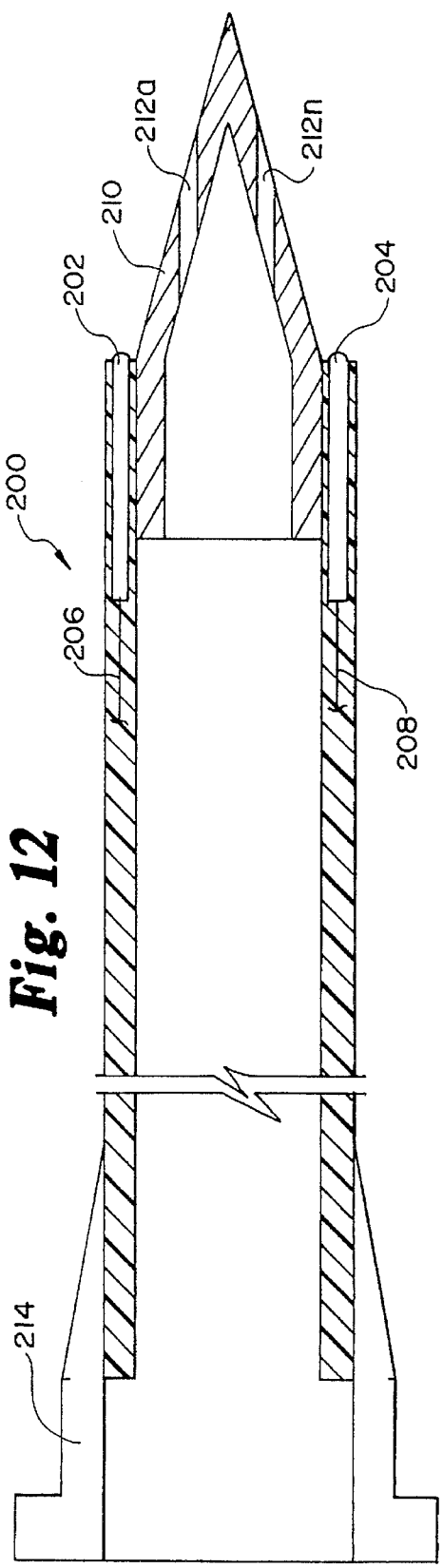

ABLATION CATHETER SYSTEM

CROSS REFERENCES TO CO-PENDING APPLICATIONS

This s a continuation of application Ser. No. 07/913,380, filed Jul. 15, 1992 which is now abandoned.

BACKGROUND OF THE INVENTION

1. Field of the Invention

The present invention is for a catheter system, and more particularly, pertains to a system of a mapping and guiding catheter and an ablation catheter for use in the mapping and guiding catheter for treatment of tachyarrhythmia.

2. Description of the Prior Art

Ablation of myocardial tissue as it is practiced today has several problems.

First, the identification of the correct arrythmogenic site is both difficult and time consuming. Thus, once the correct site is found, it is advantageous to keep this location at all costs. The constant motion of the heart may make some positions difficult to hold.

Second, current ablation procedures perform both mapping and ablation with the same catheter. Many times, blood is coagulated onto the electrodes during ablation, necessitating the removal of catheter from the heart for cleaning. This results in the loss of position, necessitating another mapping period to find the correct site.

Third, most catheter systems do not measure the response of myocardial tissue to the application of energy. As a result, it is sometimes difficult to know whether the tissue is being destroyed or whether the energy is being diverted to the catheter or blood. This may cause procedures to take longer or have unwanted side effects to the patient.

The present invention overcomes these problems. The catheter system is divided into two separate devices. The first device is a mapping/guiding catheter, which has the ability to perform local activation mapping and to guide an ablation catheter to its target site. The second device is an ablation catheter which delivers energy to the myocardium to destroy selected myocardial tissue.

SUMMARY OF THE INVENTION

Tachyarrhythmia is a form of cardiovascular disease in which the normal rhythm of the heart is accelerated leading to physiological symptoms and possibly death. Treatments for tachyarrhythmia include drugs, implantable devices, surgery and catheter ablation. The first two methods manage the disease, while the latter two try to effect a "cure" in that the underlying reason for the tachyarrhythmia is eliminated.

Catheter based ablation offers the ability to "cure" the patient with risks comparable to that of coronary angioplasty. For patients whose disease is amenable to such treatment, catheter-based ablation is becoming the therapy of choice. Generally, these patients have readily identifiable regions in the heart which are causing the tachyarrhythmia. Catheters are then used to identify these regions and then to destroy the electrophysiological properties of the tissue by heating or cooling the cells of the myocardium. The structure of the heart muscle is preserved while the conduction pathways are altered.

A typical ablation procedure is divided into four phases.

During the first phase, global activation mapping is performed from the endocardium. Mapping catheters are inserted into either arteries or veins, and placed inside one of the chambers of the heart for purposes of measuring electrical potentials and stimulation. These catheters contain metallic electrodes which are connected by small wires to electrophysiological mapping equipment and electrical stimulators. In the mapping mode, the electrodes sense the electrical signals of the tissue it contacts and these signals are displayed on monitors. By acquiring signals from different electrodes and by either moving the catheter or using several catheters, the electrical conduction patterns in the heart can be identified. In the stimulation mode, electrical signals similar to those generated by the heart are sent to the catheter electrodes and the electrical response of the heart is recorded from each of the catheter electrodes. By analyzing the response of the heart to various stimuli, the region of the heart which is responsible for the tachyarrhythmia may be identified.

During the second phase, local activation mapping is done to isolate more specifically the tissue causing the tachyarrhythmia. A mapping catheter is placed in the identified region and moved in very small increments over the endocardial surface of the heart. The resulting electrical signals with and without stimulation are analyzed to identify the exact site for tissue ablation.

During the third phase, energy is applied to the identified tissue to destroy its electrophysiological properties. This may take the form of heat via electromagnetic energy or cold via cryogenic fluids. Once the myocardial cells are destroyed, they no longer can conduct electrophysiological signals. Thus, if the mapping has identified the true arrythmogenic tissue, the tachyarrhythmia is eliminated.

During the fourth phase, the global activation of phase one is repeated to confirm elimination of the tachyarrhythmia.

Significant aspects and features of the present invention include a guiding and mapping catheter which can be utilized with any ablation catheter, which moves inside the heart, either the ventricle or the atrium, which is used to identify a specific myocardial tissue, which can maintain the identified position over a period of time, and which can accommodate an ablation catheter through a central lumen. The guiding/mapping catheter can either be flexible or rigid, and may have steering to assist in positioning.

Another significant aspect and feature of the present invention is an ablation catheter which monitors the tissue properties in response to the ablation, which provides for control the ablation energy, which monitors the heart signals for local activation times, which monitors other tissue properties in response to the ablation, including temperature, the spectral characteristics and the electrical properties of tissue, and which includes the ability to provide wash solutions to keep biological or blood products out of the field of view of the ablative energy. The particular ablation catheter can utilize a laser, RF, ultrasonic, or microwave energy source, or may use chemical fluids, toxic to myocardial cells.

Having thus described the embodiments of the present invention, it is a principal object hereof to provide a catheter system, including a guiding/mapping catheter which can also receive an ablation catheter, such as a laser ablation catheter.

One object of the present invention is a guiding/mapping catheter which moves inside the heart, identifies an active site, and holds a position at the active site.

Another object of the present invention is an ablation catheter which monitors the tissue properties in response to the ablation.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 illustrates a plan view of a guiding and mapping catheter;

FIG. 2 illustrates an end view of the tip;

FIG. 3 illustrates a plurality of ring electrodes about the tubular guiding catheter member;

FIG. 4 illustrates the guiding and mapping catheter with mechanical steering;

FIG. 9 illustrates a plan view of the guiding and mapping catheter accommodating an ablation catheter;

FIG. 10 illustrates a cross-sectional view of an RF ablation catheter, a first alternative embodiment;

FIG. 11 illustrates a cross-sectional view of a microwave ablation catheter, a second alternative embodiment; and, FIG. 12 illustrates a cross-sectional view of a chemical ablation catheter, a third alternative embodiment.

DESCRIPTION OF THE PREFERRED EMBODIMENTS

Figure 5A:
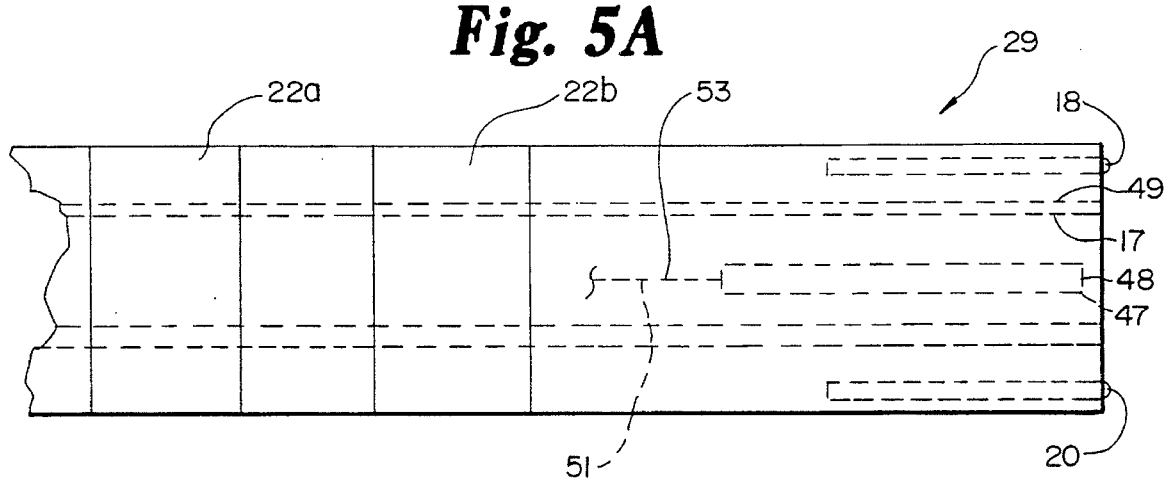
FIG. 5A illustrates a side view of the end of the guiding and mapping catheter with electrical steering.

FIG. 1 illustrates a plan view of a guiding/mapping catheter 10 and includes aligned Y-adapters 12 and 14. A tubular guiding catheter member 16 of braid reinforced plastic tubing extends through the Y-adapters 12 and 14, and contains a central lumen 17 which is large enough to pass an ablation catheter and to permit continuous flush of saline while in the body. The tubular guiding catheter member 16 itself contains two pin-like electrodes 18 and 20 at the very tip 29 and a multiplicity of ring electrodes 22a–22n perpendicular to its longitudinal axis as also illustrated in FIGS. 4 and 5. These electrodes provide for local activation mapping. The guiding/mapping catheter 10 also contains a movable fixation wire 24 for attaching the tip 29 of the tubular guiding catheter member 16 to the myocardium once the desired position for the tip 29 is found. This fixation wire 24 is activated at a port 26 of the Y-adapter 12 by a syringe 28 or comparable assembly. The Y-adapters 12 and 14 and associated members of the guiding/mapping catheter 10 provide for all mechanical, electrical and hydraulic interfaces, as well as irrigation.

The guiding/mapping catheter 10 has the capability to articulate its tip 29 such that the tip 29 can be maneuvered around within a given chamber of the heart. Such articulation can be comprised of an external or internal member. FIG. 1 shows an external system whereby a stiff sheath 30 is placed over the outside of the tubular guiding catheter member 16 to straighten out and support the tubular guiding catheter member 16. The tubular guiding catheter 16 conforms with the path of the artery or vein, or, in the alternative, can be preshaped to align with a particular arterial path. By controlling the relationship between the tubular guiding catheter member 16 and the sheath 30, many different positions of the tip 29 can be obtained.

Alternatively, the articulation mechanism can be internal to the tip of the guiding/mapping catheter, as illustrated in FIGS. 4 and 5, and can be activated by a mechanical or electrical means.

The guiding/mapping catheter 10 includes tip electrodes, ring electrodes and associated conducting wires, as also illustrated in FIGS. 2 and 3. The tip 29 of the guiding/mapping catheter 10 is made of plastic. A pair of stainless steel electrodes 18 and 20 are housed in the tip 29 as also illustrated in FIG. 4. The tip 29 is attached to a braid-reinforced plastic tubing, which comprises the tubular guiding catheter member 16, with a central lumen 17 for the laser catheter. This braided tubing provides a flexible and torqueable guide for the laser catheter described in FIG. 6. The electrode wires between the electrode interface cable 16 and the ring electrodes 22a and the top electrodes 18 and 20 are incorporated into a spiral-wound wrap. The braided tubing is attached to a Y-adapter 12, that provides an interface for the electrodes, and a luer fitting for a Tohey-Borst-type swivel adapter. The guiding/mapping catheter deflecting sheath 30 is comprised of a long TEFLON tube attached to the Y-connector 14. This Y-connector 14 contains a port for irrigating fluid and a Tohey-Borst-type gasket to seal around the tubular guiding catheter member 16. Also included are an ablation catheter port 32 and an irrigation port for the Y-adapter 12, an irrigation port 34 for the sheath 30 on the Y-adapter 14, and an electrode interface 36 and cable 38 intersecting the tubular guiding catheter member 16.

FIG. 2 illustrates an end view of the tip 29 where all numerals correspond to those elements previously described. Illustrated in particular are the pin electrodes 18 and 20 and the fixation wire 24 located and aligned in the walls of the tubular guiding catheter member 16 with a through lumen 17.

FIG. 3 illustrates a plurality of ring electrodes 22a–22n about the tubular guiding catheter member where all numerals correspond to those elements previously described.

FIG. 4 illustrates the end of the guiding and mapping catheter 10 having mechanical steering. The mechanical steering includes at least one wire 25 which extends from a steering ring 27 in the tip 29 of the catheter to the Y-adapter 14 and are contained in at least one tube 40 in the wall of the tubular guiding catheter member 16. The wire or wires are pulled to move the distal tip 29 of the guiding catheter 10. Wires 42 and 44 are illustrated connecting the pin electrodes 18 and 20. A plurality of wires 46a and 46n are also illustrated connecting to the plurality of ring electrodes 22a–22n. Wires 42, 44 and 46a–46n secure appropriately to the electrode interface 36 via cable 38 of FIG. 1.

Figure 5B:
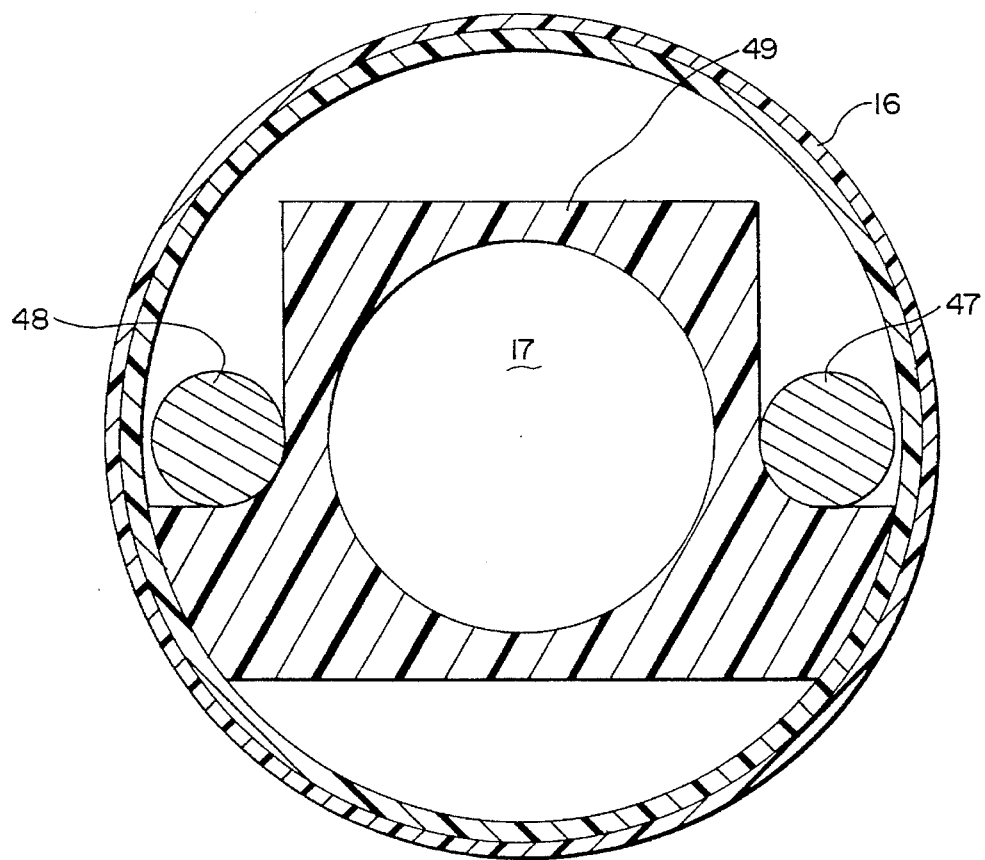
FIG. 5B illustrates a view in cross section of the end of the guiding and mapping catheter with electrical steering.

FIG. 5A illustrates a side view of the end of the guiding and mapping catheter 10 with electrical steering where all numerals correspond to those elements previously described. The electrical system, includes memory shaped metals or alloys which are heated and shaped by increasing the temperature of the metals or alloys by the introduction of electrical currents. These memory shaped metals include a shaping element 47 and a retracting element 48 placed adjacent to a central member 49 containing the central lumen 17, as illustrated in FIG. 5B. Wires 51 and 53 connect to the shaping element 47 and retracting element 48 and are routed to the electrode interface 36 of FIG. 1.

FIG. 5B illustrates a view in cross section of the end of the guiding and mapping catheter 10 with electrical steering where all numerals correspond to those elements previously described.

Figure 6:
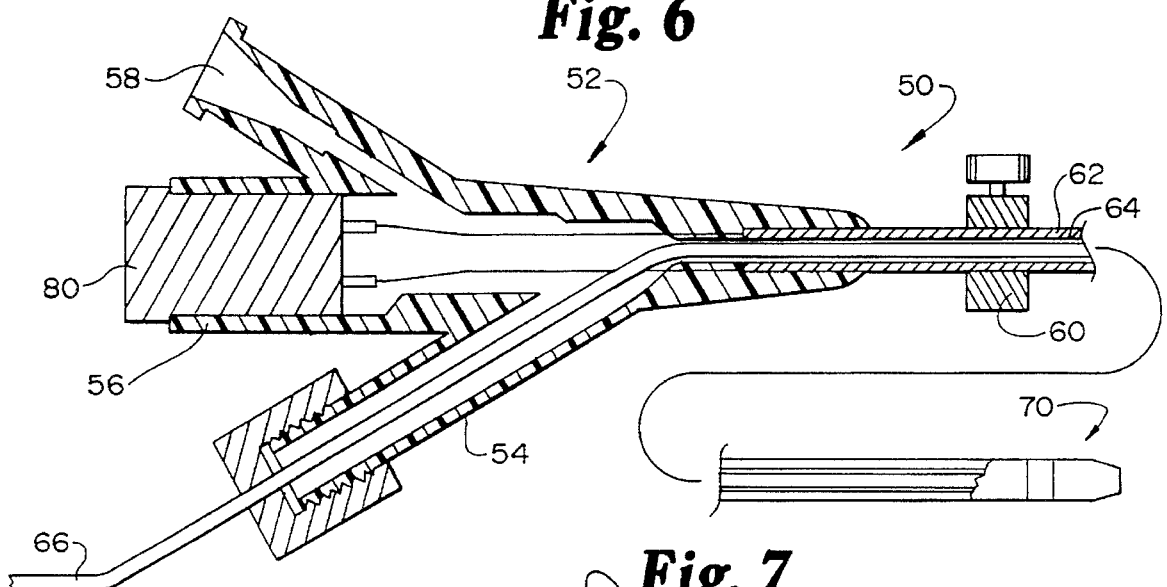
FIG. 6 illustrates a plan view of an ablation catheter in partial cross section.
Figure 7:
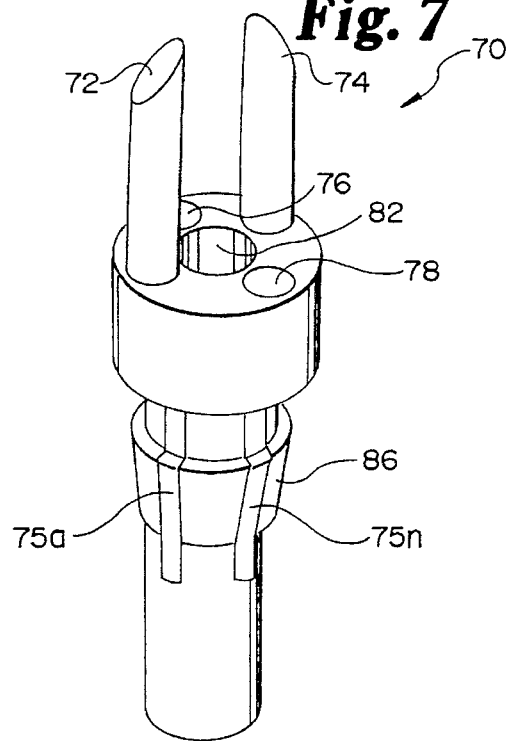
FIG. 7 illustrates a perspective view of the ablation catheter tip.

FIG. 6 illustrates a plan view of an ablation catheter 50 in partial cross section. This catheter includes a y-adapter 52 having an energy delivery port 54, an electrical connection port 56, an irrigation port 58, a catheter stop 60, a plastic tubular member 62 having a central lumen 64 for passage of an ablative energy delivery member 66 which may be an optical fiber as is the case with laser energy sources, or in the alternative, can be an insulated copper wire such as with RF energy, or a coaxial cable for the delivery of microwave energy. The plastic tubular member 62 and lumen 64 accommodate the ablative energy delivery member 66, and also channels fluid to the point of contact of the energy delivery member with the myocardial tissue. The ablation energy delivery member 66 is appropriately sized to allow passage of liquid between it and the walls forming the lumen 64 for passage of the tip 70. At the configured tip 70 of the catheter 50 are embedded sensing elements, which penetrate the myocardial tissue. For purposes of illustration, two metallic needles 72 and 74 are shown in FIG. 7, each of which contains a thermocouple for measuring tissue temperature. The needles 72 and 74 also act as fixation elements to hold the position of the ablation catheter 50 during ablation. The fixation device could also be a separate part of the catheter which would run along side of the central lumen 64, and may be movable by a mechanism at the Y-adapter 52 of the ablation catheter 50. Also embedded in the tip 70 of the ablation catheter 50 are pin electrodes 76 and 78 for measuring local activation electrical signals. These electrodes help to confirm the position of the ablation catheter 50, as well as establish the degree of contact of the tip 70 with the endocardial surface.

All interfaces are brought to the proximal Y-adapter 52 of the ablation catheter 50 for connection to other medical devices. The electrode wires are interfaced through a quick disconnect fitting 80, which then connects to standard EP monitoring and temperature measuring equipment. The irrigation port 58 uses a standard luer fitting which connects to an infusion pump capable of displacing the needed amount of saline solution. The ablation energy delivery member 66 connects to source generator, which could be radio frequency, microwave, laser or any other source which can destroy myocardial tissue.

The outer diameter of the laser catheter plastic tubing sheath 68 is such that it will fit down the internal lumen 17 of the mapping/guiding catheter 10 of FIG. 1.

Figure 8:
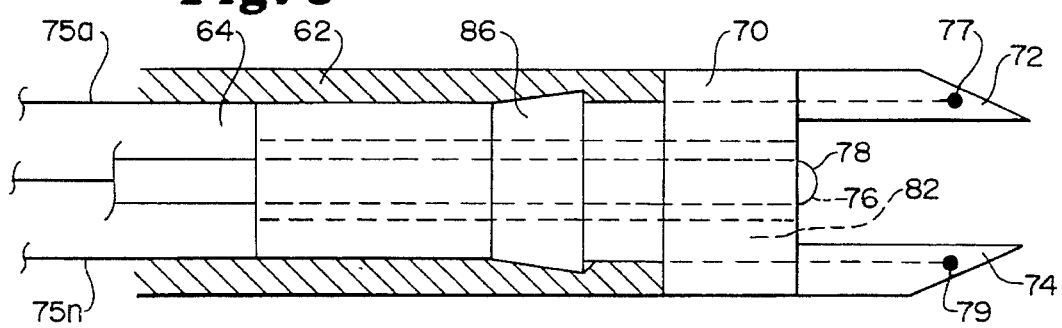
FIG. 8 illustrates a view in partial cross section of the ablation catheter tip.

The body of the laser catheter 50 includes the following components as now described in detail, and also illustrated in FIG. 7 and 8. A plastic tube 62 provides central lumen 64 for internal components and flushing fluid. A stainless steel tip 70 is attached to the distal end of the plastic tube 62. The tip 70 is comprised of a through lumen 82 for placement and fixation of a single ablative energy delivery member 66, two small stainless steel hypodermic tubes/needles 72 and 74 that contain one thermocouple each, a plurality of small slots 84a–84n for irrigating the tip of ablative energy delivery member 66, and two stainless steel electrodes 76 and 78 for sensing electrical signals. The ablative energy delivery member 66 when used in the form of an optical fiber has a silica core, polymer clad, with a TEFLON jacket. The optical fiber extends beyond the tip 70 and is held in place in the metallic tip by a mechanical crimp 86. The annular space between the optical fiber (ablative energy delivery member 66) and the stainless steel wall of the tip 70 serves as a conduit for irrigating fluid, such as saline, which both cools the tissue and purges blood from the delivered energy field during irradiation by the desired energy delivery member 66. A thermocouple is soldered inside each hypodermic tubes or needles 72 and 74 near the distal end. The hypodermic tubes or needles 72 and 74 are soldered to the metallic tip 70; thus, the spatial relationship between the thermocouples and the distal face of the optical fiber is fixed. The thermocouples are standard types and the signals are carried to a temperature data acquisition and control system by small-diameter TEFLON-coated wire routed through the catheter tube 62 and the fitting/interface 80 in the laser catheter y-adapter 52. The two stainless steel electrodes 76 and 78 are positioned opposite each other on the distal face of the tip 70 to sense electrical signals. These electrodes are insulated from the bulk of the tip 70 by polymide tubing. EP signals are carried from these electrodes 76 and 78 to standard EP mapping equipment by small-diameter TEFLON-coated wire routed through the catheter tube and a connector in the laser catheter y-adapter 52. A molded plastic y-adapter 52 at the proximal end of the tubular member 62 contains an interface fitting for the temperature and EP monitoring systems, a port 58 for irrigating fluids, and the ablative energy delivery member 66. The ablation energy member extends 2 meters beyond the handle and is terminated with standard connectors, which mate with the ablative energy source.

FIG. 7 illustrates a perspective view of the tip 70 where all numerals correspond to those elements previously described. Illustrated in particular are the needles 72 and 74 each having embedded thermocouples. A plurality of flat wire leads 75a–75n connect to the needles 72 and 74 and to the electrodes 76 and 78 for subsequent wire connection to the electrode interface 80.

FIG. 8 illustrates a side view in partial cross section of the tip 70 where all numerals correspond to those elements previously described. Thermocouples 77 and 79 are embedded in the needles 72 and 74, respectively.

FIG. 9 illustrates a plan view of the guiding and mapping catheter 10 accommodating the ablation catheter 50 where all numerals correspond to those elements previously described.

MODE OF OPERATION

The mode of operation of this ablation catheter system is such that the guiding/mapping catheter 10 of FIG. 1 is placed in one of the chambers of the heart using standard angiographic techniques. This would normally include use of a guide wire to insure that no perforation of the vasculature occurs. The tip of the guiding/mapping catheter 10 is then placed in contact with the endocardial surface of the heart such that the tip 29 of the guiding/mapping catheter 10 is perpendicular to the heart wall. The electrical signals from the two electrodes 18 and 20 embedded in the tip 29 are then analyzed and recorded as both unipolar and bipolar signals. The catheter tip 29 is then be moved to another site on the endocardial surface using the steering mechanism. Positioning and subsequent analysis is continued until the desired location is identified. The fixation wire 24 is then activated attaching the tip 29 of the guiding/mapping catheter 10 to the endocardial surface of the heart.

The primary functions of the guiding/mapping catheter 10 assembly is to identify the location of tachyarrhythmia sites through electrical activation mapping, and to mechanically guide the ablation catheter 50 to the desired irradiation sites.

The guiding/mapping catheter electrodes 18, 20, and 22a–22n are coupled to standard hospital EP mapping equipment.

The deflecting sheath 30 can be used to direct the distal tip 29 of the guiding/mapping catheter 10 by advancing the distal end of the deflecting sheath 30 toward the tip 29 of the guiding/mapping catheter, thereby straightening the curve. Deflecting sheath 30 advancement and return is accomplished by moving the deflecting sheath Y-connector 14 while maintaining the position of the tubular guiding catheter member 16.

Standard hospital continuous-flow fluid pumps with flow monitoring capabilities are used to provide sterile saline irrigation for the guiding/mapping catheter 10.

The ablation catheter of FIG. 6 is then inserted into the guiding/mapping catheter 10 much like a balloon angioplasty catheter is inserted into a standard guiding catheter as illustrated in FIG. 9. The ablation catheter 50 is flushed with saline to keep blood and other biological tissue out of the field of view of the ablation catheter 50. The ablation catheter is then moved forward until it comes in contact or near contact with the endocardial surface. The fixation element and tip electrode then engage the myocardium and the ablation energy source is prepared for activation.

The ablation source is used until the desired tissue damage is accomplished. The monitoring is continuous and the ablations source interrupted if a situation develops in which continued use of the ablative energy could damage either the catheter or the myocardium. This may be accomplished manually or by an automated system interfaced to the ablative energy source.

DESCRIPTION OF THE FIRST ALTERNATIVE EMBODIMENT

FIG. 10 illustrates a cross-sectional view of an RF ablation catheter 100, a first alternative embodiment. Another embodiment is to use a standard RF catheter through an open catheter port 32 and lumen 17 through the center for ablation. A fixation and monitoring wire is passed down the center of the ablation catheter 100 for purposes of stabilization of the catheter during ablation and monitoring of tissue response.

The RF ablation catheter 100 with monitoring capabilities is consistent with and incorporates the teaching of the present invention as previously described for use with an RF generator and y-adapters of the previous embodiments.

One of the dangers inherent in any ablation system is destruction of healthy tissue which is not part of the tachycardia. It is desirable to keep this collateral damage to a minimum so as to maximize the therapeutic value of this treatment. One way to minimize this damage is to monitor the effect of the energy on the myocardial tissue being irradiated. Such monitoring can be done by measuring tissue temperature, changes in optical properties of the tissue, or changes in electrical patterns of the tissue.

An extension of the basic invention is to add the ability to monitor tissue response to RF irradiation. This is done via thermocouples placed at the surface or in the tissue, optical fibers placed in contact with the myocardium, or small electrodes placed in contact with the endocardial surface.

To accommodate these additional elements, the RF ablation catheter 100 has a lumen through it. Such a lumen can be centered or offset. Depending on the type of monitoring, the additional elements are terminated so as to interface with commercially available monitoring equipment.

An additional feature which could be added to this system would be the use of feedback to control the input of energy to optimize the elimination of the tachycardia. The monitoring system would be connected to a system in which the signals can be continuously monitored and changes made in the energy inputted into the catheter. Such a system could be as simple as an on/off controller which turns the energy off above a specified value and on below a specified value. The system could be as complex as a microprocessor in which the signals are analyzed more complexly and the rates of change or signal patterns incorporated into the decision process.

The illustrated RF ablation catheter 100 has like and corresponding members relating expressly to previously described members which operate and are conceived in the same fashion, including mapping band electrodes 102 and 104, an internal coaxial cable 106, consisting of a center conductor antenna 108, an external conductor of either solid or braid serving as a shield 110, and dielectric material 111 and a covering 113, a signal wire lumen 112 extending to the distal tip 116, signal wires 118 and 120 connected to the mapping electrodes 102 and 104, and a plastic sheath 122 placed over and about the distal end of the center conductor antenna 108. Thermocouples 124 and 126 are placed near the distal end of the RF antenna radiator 108 having wires (not illustrated for purposes of brevity and clarity) which pass outwardly for external measurement and analysis.

Another problem with catheters placed in a beating heart is that these catheters may be moved around by the mechanical action of the heart, thus irradiating undesirable area. One solution is to fixate the catheter via an integral fixation system. Such a system attaches to the wall of the heart and holds the catheter in its proper location in the heart. Such a system is activated once the proper location is found in the heart.

A fixation system wire 128 passes through the length of the RF ablation catheter 100 and through lumen 130, and consists of a type of wire with a special pointed end 131. The pointed end 131 is inserted into the myocardium. This system holds the RF ablation catheter 100 as a fixed surface location. A more complex system would be a helical coil which would be screwed into the heart muscle. This system would provide perpendicular, as well as lateral fixation. Alternatively, thermistors, thermocouples or optical temperature sensors 132 and 134 can be included in the fixation system wire 128 for temperature sensing of and about heart tissues in close proximity to the antenna radiator 108. The thermistor wires are not fully illustrated for purposes of brevity and clarity.

DESCRIPTION OF THE SECOND ALTERNATIVE EMBODIMENT

FIG. 11, a second alternative embodiments, illustrates a cross-sectional view of microwave ablation catheter 150 with monitoring capabilities which is consistent with and incorporates the teaching of the present invention as previously described for use with the microwave generator and y-adapters of the previous embodiment.

One of the dangers inherent in any ablation system is destruction of healthy tissue which is not part of the tachycardia. It is desirable to keep this collateral damage to a minimum so as to maximize the therapeutic value of this treatment. One way to minimize this damage is to monitor the effect of the energy on the myocardial tissue being irradiated. Such monitoring can be done by measuring tissue temperature, changes in optical properties of the tissue, or changes in electrical patterns of the tissue.

An extension of the basic invention is to add the ability to monitor tissue response to microwave irradiation. This is done via thermocouples placed at the surface or in the tissue, optical fibers placed in contact with the myocardium, or small electrodes placed in contact with the endocardial surface.

To accommodate these additional elements, the catheter has a lumen through it. Depending on the type of monitoring, the additional elements would be terminated so as to interface with commercially available monitoring equipment.

An additional feature which could be added to this system would be the use of feedback to control the input of energy to optimize the elimination of the tachycardia. The monitoring system would be connected to a system in which the signals can be continuously monitored and changes made in the energy inputted into the catheter. Such a system could be as simple as an on/off controller which turns the energy off above a specified value and on below a specified value. The system could be as complex as a microprocessor in which the signals are analyzed more complexly and the rates of change or signal patterns incorporated into the decision process.

The illustrated microwave ablation catheter 150 has like and corresponding members relating expressly to previously described members which operate and are conceived in the same fashion, including mapping band electrodes 152 and 154, an internal coaxial cable 156, consisting of a center conductor 160, an external conductor either solid or braid serving as a shield 158, and dielectric material 162, a signal wire lumen 164, a lumen 166 extending through a distal tip 167, signal wires 168 and 170 connected to the mapping band electrodes 152 and 154, a microwave antenna coil 172, a plastic sheath 173, and other corresponding members. Thermocouples 174 and 176 are placed near the microwave coil 172 having wires (not illustrated for purposes of brevity and clarity) which pass outwardly through the signal wire lumen 164 for external measurement and analysis.

Another problem with catheters placed in a beating heart is that these catheters may be moved around by the mechanical action of the heart, thus irradiating undesirable areas. One solution is to fixate the catheter via an integral fixation system. Such a system attaches to the wall of the heart and holds the catheter in its proper location in the heart. Such a system is activated once the proper location is found in the heart.

A fixation system wire 178 passes through the length of the microwave ablation catheter 150 and through lumen 166, and consists of a type of wire with a special pointed end 180. The pointed end 180 is inserted into the myocardium. This system holds the microwave ablation catheter 150 at a fixed surface location. A more complex system would be a helical coil which would be screwed into the heart muscle. This system would provide perpendicular, as well as lateral fixation. Alternatively, thermistors or thermocouples or optical temperature sensors 182 and 184 can be included in the fixation system wire 178 for temperature sensing of and about heart tissues in close proximity to the microwave antenna coil 172. The thermistor wires are not fully illustrated for purposes of brevity and clarity, but route through the fixation wire 178.

DESCRIPTION OF THE THIRD ALTERNATIVE EMBODIMENT

FIG. 12 illustrates a cross-sectional view of a chemical ablation catheter 200, a third alternative embodiment. In the chemical ablation catheter 200, a needle 210 pierces myocardium and chemical such as ethanol is injected into myocardium, while the guiding/mapping catheter is being flushed. Pin electrodes 202 and 204 are located at the distal end of the ablation catheter 200 and include connection wires 206 and 208 leading to external connector blocks. The needle 210 located at the distal end includes a plurality of ports 212a–212n for injection of liquid ablation chemicals into the myocardium. A luer connector 214 connects to an external drug pump.

Various modifications can be made to the present invention without departing from the apparent scope hereof.

I claim:

1. A guiding/mapping catheter for use with heart tissue, comprising:
   (a) a catheter body comprising a central lumen and a non-collapsible tip structure comprising a distal end;
   (b) a plurality of electrodes positioned within the catheter body to communicate with tissue at the distal end of the tip structure, for finding arrythmogenic tissue in planar and non-planar tissue surfaces at an identified location via local activation mapping;
   (c) monitor means, operatively coupled to the plurality of electrodes, for identifying the arrythmogenic tissue; and
   (d) maneuvering means, within the tip structure, for movement of the catheter along the tissue surface.

2. The guiding/mapping catheter of claim 1 further comprising means for affixing to the wall of the tissue to hold the identified location.

3. The guiding/mapping catheter of claim 1 further comprising means for receiving an ablative catheter down the central lumen.

4. The guiding/mapping catheter of claim 3 further comprising flushing means for providing a fluid which baths a contact point of the ablative catheter with the tissue to keep biological material out of a field of influence of the ablative catheter.

5. A catheter system for use with heart tissue, comprising:
   (a) a guiding/mapping catheter, comprising:
      (i) a catheter body comprising a central lumen and a non-collapsible tip structure comprising a distal end;
      (ii) a plurality of electrodes positioned within the catheter body to communicate with tissue at the distal end of the tip structure for finding arrythmogenic tissue in planar and non-planar heart tissue surfaces at an identified location via local activation mapping;
      (iii) monitor means, operatively coupled to the plurality of electrodes, for identifying the arrythmogenic tissue; and
      (iv) maneuvering means, within the tip structure, for movement of the catheter along the tissue surface; and
   (b) an ablation catheter operatively configured for positioning within the central lumen of the guiding/mapping catheter, the ablation catheter comprising:
      (i) a catheter body having a proximal end and a distal end;
      (ii) a tip structure attached at the distal end of the catheter body;
      (iii) ablative means in said catheter body for providing ablative energy to the arrythmogenic tissue; and
      (iv) tissue sensing means for measuring directly the effect of the ablative energy on the arrythmogenic tissue.

6. The catheter system of claim 5 wherein the guiding/mapping catheter further includes fixation means for fixating the guiding/mapping catheter to the heart tissue to hold the guiding/mapping catheter at the identified location.

7. The catheter system of claim 5 including means for flushing to keep biological material out of a field of influence of the ablation catheter.

8. The catheter system of claim 5 wherein the guiding/mapping catheter further includes means for receiving the ablative catheter down the central lumen of the guiding/mapping catheter.

9. The catheter system of claim 5 wherein the guiding/mapping catheter further includes means for articulating the distal end of the guiding/mapping catheter inside the heart to move perpendicularly along the wall of the heart.

10. The catheter system of claim 5 further comprising flushing means for providing a flushing fluid which baths a contact point of the ablation catheter with the heart tissue to prevent coagulation of blood and other biological material proximate the contact point.

11. The catheter system of claim 5 wherein the ablation catheter further includes means for measuring the local activation such that an electrophysiological potential of the heart tissue can be monitored.

12. The catheter system of claim 5 wherein the ablation catheter tissue sensing means comprises an integral fixed mechanism for attaching the catheter system to a wall of the tissue.

13. The catheter system of claim 5 wherein the ablation catheter is operatively configured for easy insertion and removal from the guiding/mapping catheter without losing the identified location for ablation.

14. The catheter system of claim 5 wherein said ablative energy is selected from the group consisting of laser energy, radio frequency energy, microwave energy, and chemical energy.

15. The catheter system of claim 5 wherein said ablative energy is RF energy.

16. The catheter system of claim 5 wherein said ablative energy is microwave energy.

17. The catheter system of claim 5 wherein said ablative energy is chemical energy.

18. The guiding/mapping catheter of claim 1 further comprising maneuvering means external to the catheter body.

19. The catheter system of claim 5 wherein the ablation catheter tissue sensing means comprises an integral movable mechanism for attaching the catheter system to a wall of the tissue.

20. The catheter system of claim 5 wherein the ablation catheter tissue sensing means comprises at least one temperature sensor.

21. A catheter system comprising:
   (a) a guiding/mapping catheter comprising:
      (i) a central lumen extending through the guiding/mapping catheter;
      (ii) a tip at an end of the guiding/mapping catheter; and
      (iii) at least one electrode positioned to communicate with tissue at the tip to find arrythmogenic tissue in tissue surfaces at an identified location via local activation mapping; and
   (b) an ablation catheter removably inserted within the central lumen of the guiding/mapping catheter, the ablation catheter comprising:
      (i) a catheter body having a distal end;
      (ii) a tip at the distal end to provide ablative energy to the arrythmogenic tissue; and
      (iii) a tissue sensing device to measure the effect of the ablative energy on the arrythmogenic tissue.

22. The catheter system of claim 21, wherein the ablation catheter comprises at least one pin electrode and at least one sensing element disposed at the tip of the ablation catheter.

23. The catheter system of claim 21, wherein the guiding/mapping catheter comprises a fixation element to fix the guiding/mapping catheter to the tissue and to hold the guiding/mapping catheter at the identified location.

24. The catheter system of claim 21, wherein the guiding/mapping catheter comprises a plurality of electrodes positioned within the catheter body.

\* \* \* \* \*